United States Patent [19]
Guinee et al.

[11] Patent Number: 6,139,889
[45] Date of Patent: Oct. 31, 2000

[54] APPARATUS AND METHOD FOR THE QUANTIFICATION OF THE STRETCHABILITY OF CHEESE

[75] Inventors: Timothy P. Guinee; Donal J. O'Callaghan, both of County Cork, Ireland

[73] Assignee: Teagasc, The Agriculture and Food Development Authority, Dublin, Ireland

[21] Appl. No.: 09/254,047

[22] PCT Filed: Aug. 22, 1997

[86] PCT No.: PCT/IE97/00061

§ 371 Date: Mar. 1, 1999

§ 102(e) Date: Mar. 1, 1999

[87] PCT Pub. No.: WO98/09149

PCT Pub. Date: Mar. 5, 1998

[30] Foreign Application Priority Data

Aug. 30, 1996 [IE] Ireland ................................. S960615

[51] Int. Cl.[7] ............................. G01N 33/04; G01N 3/08
[52] U.S. Cl. ........................... 426/231; 426/478; 426/518
[58] Field of Search ..................... 426/231, 582, 426/478, 518

[56] References Cited

FOREIGN PATENT DOCUMENTS

| | | |
|---|---|---|
| 2 280 272 | 1/1995 | United Kingdom . |
| 88/04418 | 6/1988 | WIPO . |
| 90/08306 | 7/1990 | WIPO . |

OTHER PUBLICATIONS

C. Apostolopoulos, "Simple empirical and fundamental methods to determine objectively the stretchability of Mozzarella cheese", Journal of Dairy Research, vol. 61, 1994, pp. 405–413.

*Primary Examiner*—Milton Cano
*Attorney, Agent, or Firm*—Young & Thompson

[57] ABSTRACT

An apparatus and method for quantifying the stretchability of molten cheese, typically mozzarella cheese, on a pizza pie. The apparatus includes a first platform (1) having clamp (11) of which one part (7) of the pizza base is affixed to the first platform (1). The other part (8) of the pizza base is affixed to a second platform (2) by a clamp (12). The second platform (2) is mounted on a wheeled bogey which is drawn along rails by a winch driven by an electric motor for moving the second platform (2) relative to the first platform (1), at a constant velocity, in a horizontal plane, to draw the two parts (7, 8) of the pizza base apart thereby stretching the mass of cheese into strands (13). Elements are provided for measuring the distance traveled by the second platform (2) at breakage of the cheese strands.

9 Claims, 6 Drawing Sheets

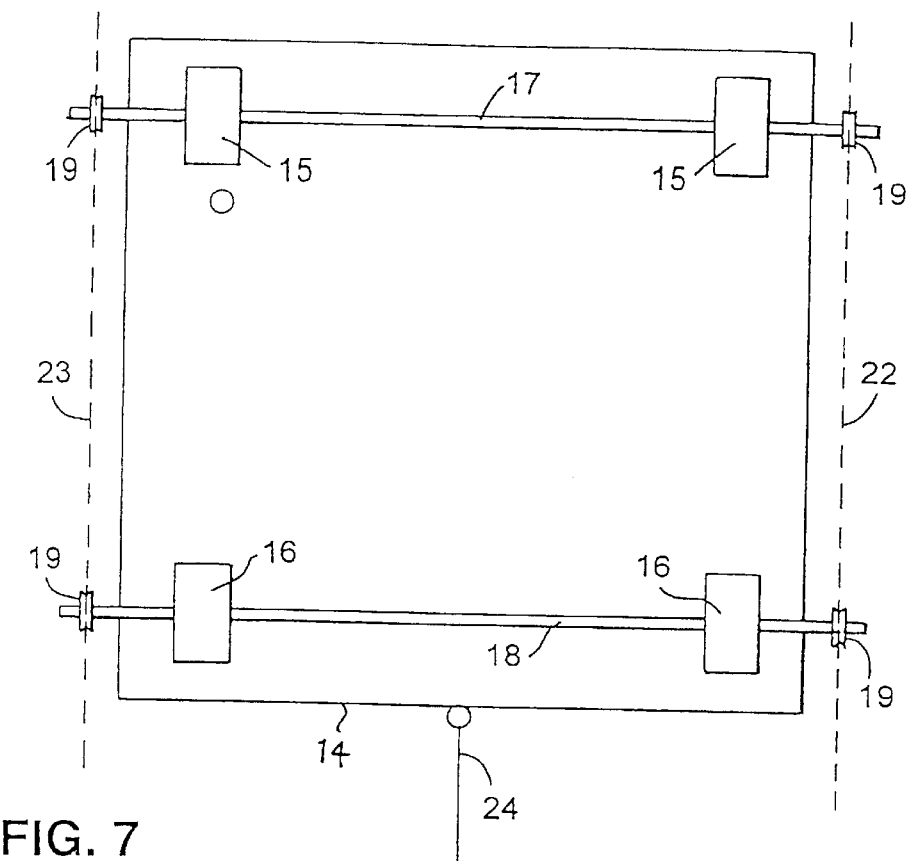
FIG. 7
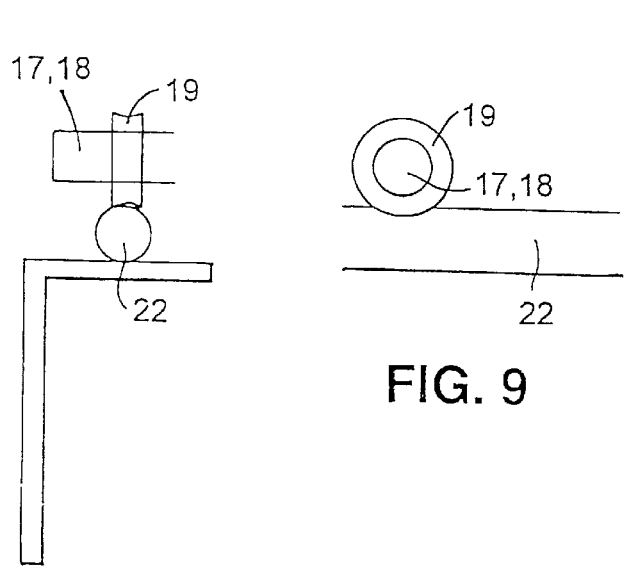
FIG. 8
FIG. 9
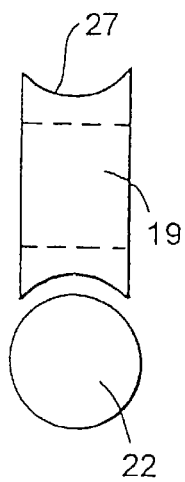
FIG. 10

Diagram III

APPARATUS AND METHOD FOR THE QUANTIFICATION OF THE STRETCHABILITY OF CHEESE

This application is a 371 of PCT/IE97/00061 filed Aug. 22, 1997.

FIELD OF THE INVENTION

The invention relates to an apparatus and method for the quantification of the stretchability of cheese. The invention is particularly concerned with the measurement of the stretchability of mozzarella type cheese for use on cooked pizza pies.

BACKGROUND OF THE INVENTION

Mozzarella cheese production has grown considerably in recent years, especially in the USA, where current annual production, at circa 938,000 tonnes, amounts to circa 29% of total U.S. cheese manufactured (McMahon et al., 1993; Residuary Milk Marketing Board, 1995; Personal communication, 1996—Michael Hickey, Member of IDF Group D31). This markedly exceeds that of Italy (i.e. 150,000 tonnes), the country of origin and world's second largest producer. The growth rate has been slower elsewhere but is now escalating, with significant expansion in Ireland, Denmark and New Zealand. The impetus for the dynamic growth of Mozzarella consumption has been the growing popularity of pizza pie, i.e. baked dough pie covered with cheese, tomato puree and other adjuncts such as salami and mushroom. The main type of Mozzarella used in this application is low moisture (45–52%), (USDA, 1976; Office of the Federal Register, 1986), the traditional Mozzarella (~57–60% moisture) being consumed mainly as a table cheese or as an accompaniment in salads.

The shredability of low moisture Mozzarella and its capacity to melt, flow, stretch and possess chewiness on cooking/baking make it ideal for use in pizza pies. However, its ability to stretch and form long strings when extended makes low moisture Mozzarella unique in pizza applications. Other cheeses, such as Cheddar and Provolone also have the ability to melt and flow on cooking/baking. However, these cheeses which have a relatively high level of proteolysis when mature, exhibit inferior stretch properties compared to low moisture Mozzarella. Owing to the widespread use of cheese in cooking applications, numerous studies have been undertaken vis-a-vis the development of methodology for assessing the melt, flow and consistency characteristics of cooked cheese (Arnott et al., 1957; Kosikowski, 1982; Rayan et al., 1980; Hokes et al., 1982; Park et al., 1984; Masi 1989; Kindstedt et al., 1989a, b). In contrast few investigations have dealt with the measurement of the capacity of coked molten cheese to stretch when extended. At commercial level this property is largely assessed by lifting the cooked cheese with a fork. While this method has merit in that it simulates consumer behaviour, it is very subjective as a quality control tool, as the stretchability depends on the depth to which the fork is embedded in the molten cheese mass and the rate at which it is lifted. Hence, objective methods for the determination of stretchability have appeared recently in the scientific literature (Addeo & Masi, 1992; Cavella et al., 1992; Ak et al., 1993; Apostolopoulos, 1994; Pagliarini & Beatrice, 1994; Ak & Gunasekaran, 1995). Some of these methods are based on uniaxial extension of heated cheese samples (e.g. slices, cylinders) of given dimensions using a Universal Instron-type instrument or load-cell (Ak et al., 1993; Pagliarini & Beatrice, 1994; Ak & Gunasekaran, 1995). The resulting force-displacement curves were used to determine the force required to achieve a certain displacement (i.e. stretch), the force and displacement at fracture and/or the elastic modulus and viscosity of the extended sample. The methods of Addeo & Masi, 1992 and Cavella et al. (1992), involved measurement of the force required to break a string (~1 mm thick) of melted cheese, extruded using a piston type capillary rheometer, and the percentage elongation of the string at fracture. While these methods are objective in their approach, their complexity and the operator skill required makes them somewhat unsuitable for routine rapid evaluation of stretchability. Moreover, the methods employ conditions of cheese melting (e.g. in oil bath at temperatures of 10–40° C.) and extension which do not simulate very closely those used in commercial pizza preparation and consumption.

A more empirical operator-friendly tensile test method, employing heating and stretching conditions closer to those used in practice was recently reported by Apostolopoulos (1994). Shredded cheese, at a certain loading, was placed on a pre-cut circular pizza base before heating in a microwave oven, after which the pizza was stretched. To allow a vertical stretching motion the circular cheese base was pre-cut to fit over a matching perspex disc which had a fixed annular ring and a moveable circular core with a central cross-head attachment. After loading the shredded cheese, the entire assembly (including supporting "Perspex" ™ disc) was placed in a microwave oven. On removal of the cooked pizza pie the core was attached to the cross-head of the tensile testing machine and raised at constant velocity (normally 1.5 m/min) until fracture of the cheese strings. The extensibility of the cheese, defined as the distance of travel of the cross-head until all the cheese strings failed, was used as a measure of stretchability. Details on the effects of cheese loading, the holding time of the cooked pizza before stretching and/or age and variety of cheese are not given.

WO 90/08306 discloses an apparatus and method for performing a tensile test on natural or man-made fibers such as cotton or polyester. The apparatus includes two clamps between which each end of a fiber can be clamped. One clamp is stationary while the other is associated with a tensioning device, which includes a stepping motor which is connected to the clamp by a connecting member so that by appropriate actuating of the motor, the clamp can be moved away from the stationary clamp to tension the fiber. The device monitors and measures tension force and elongation of the fiber.

OBJECT OF THE INVENTION

It is an object of the present invention ot provide a simple apparatus and method to measure objectively the stringiness/stretchability of melted cheese on cooked pizza pie, in a way resembling the manner in which the consumer stretches the cheese.

SUMMARY OF THE INVENTION

The invention provides apparatus for the quantification of the stretchability of molten cheese on a pizza pie, the molten cheese comprising a cooked mass of shredded cheese loaded onto and bridging two separated parts of an underlying pizza base, the apparatus comprising a first platform to receive one part of the pizza base, a second platform to receive the other part of the pizza base, such that the interface between the two parts of the pizza base coincides with a junction between the platforms, means for moving at least one of said platforms relative to the other platform, to draw the two parts of the pizza base apart thereby stretching the mass of cheese into strands, and means for measurement of the distance travelled by the second platform relative to the first platform, characterised in that the apparatus includes clamp means wherein the one part of the pizza base may be clamped to the first platform and the other part of the pizza base may be clamped to the second platform, and the first platform is a fixed platform and the second platform is moveable along horizontal rails, by electric motor means to cause a uniaxial extension of the melted cheese strands in a horizontal plane at constant velocity to the point of fracture of the strands. Suitably, the second platform is mounted on a wheeled bogey which may be drawn along the rails by winch means driven by an electric motor at constant velocity and optionally including a voltage-to-frequency power converter to regulate the motor speed in the range 2 to 6 m/min.

The invention also provides a method for the quantification of the stretchability of molten cheese on a pizza pie comprising the steps:

a) slicing a pizza base into two separate parts;

b) loading the adjoined parts of the pizza base with shredded cheese and cooking the pizza in an oven to form a pizza pie in which a molten mass of cheese extends over and bridges the two parts of the pizza base;

c) placing one part of the pizza base on a first platform and a second part of the pizza base on an adjoining platform.

d) moving at least one of said platforms apart relative to the other platform to stretch the mass of cheese on the parts of the pizza to form strands, said movement being carried out at a fixed velocity in a horizontal plane until the cheese strands break;

e) stopping movement of said at least one platform at the point of complete breakage of the cheese strands; and f) measuring the distance traveled by the moving platform which equates to the stretch distance of the cheese strands;

g) the respective parts of the pizza base are clamped to the respective platforms; and h) the movement of said at least one of the platforms is carried out in a horizontal plane at constant velocity to cause a uniaxial extension of the melted cheese strands to the point of fracture of the strands.

BRIEF DESCRIPTION OF THE DRAWINGS

FIG. 7 is a plan view of a sliding element of FIG. 2;

FIG. 8 is a front elevation showing a detail of a roller and rail assembly of the apparatus of FIG. 2;

FIG. 9 is a side elevation of FIG. 8;

FIG. 10 is a detail, to an enlarged scale, of the apparatus of FIG. 8;

FIGS. 12, 13 and 14 show, respectively, an alternative arrangement of the motor and pully assembly of the apparatus of FIG. 2.

DETAILED DESCRIPTION OF THE PREFERRED EMBODIMENT

Figure 1:
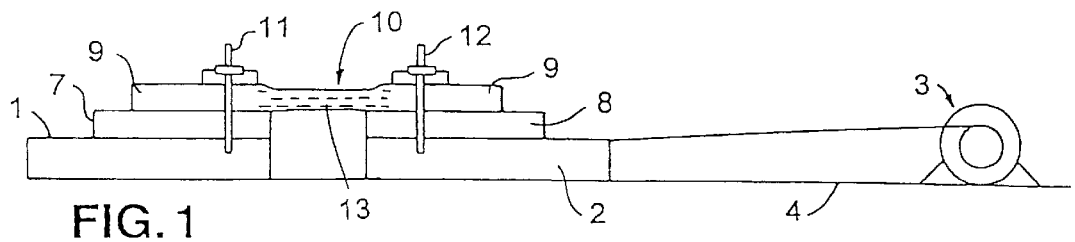
FIG. 1 is a schematic illustration of one embodiment of apparatus of the invention.

Referring firstly to FIG. 1, this is a schematic representation of the stretching of a cheese sample on a pizza base by means of the apparatus and method of the invention.

The apparatus comprises a fixed platform element 1 which lies in a horizontal plane. A moveable platform element 2 is moved by drive means 3, along horizontal guide means 4, form a first position which abuts the fixed element 1, the second position in which its cheese sample is fully stretched.

Figure 5:
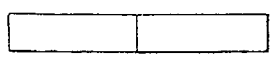
FIG. 5 is an elevation of a typical pizza base.
Figure 6:
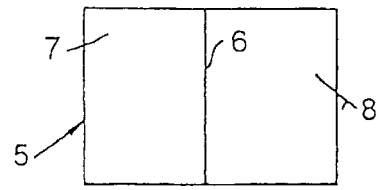
FIG. 6 is a plan view of the pizza base of FIG. 5.

In use, grated cheese is loaded, at a fixed rate onto a rectangular (e.g. 10.5 cm×15 cm) pizza base 5 (see FIGS. 5 and 6). Prior to loading the cheese, the base 5 is cut cleanly in half along a line of cut 6 comprising the short axis. The halves 7, 8 are aligned in their original position to form a flush interface. Cheese stored at 4° C., is finely grated (1–2 mm shred length) and distributed evenly over the pizza base and placed in a thermostatically-controlled electric fan oven at 280° C. for 4 min. Fine grating facilitates uniform coverage of the pizza base.

The cooked pizza pie 10 having a molten cheese layer 9 is then placed on the platform unit of the apparatus such that the interface between the two halves 7, 8 of the pizza base coincide with the junction between the fixed and moveable elements 1, 2. The ends (comprising approximately a 1.5 cm strip at the pizza edges) of the pizza pie 10 are firmly clamped to the platform elements by clamps 11, 12.

The moveable element 2 is then drawn along the guide means 4 at a fixed velocity, by the drive means 3, resulting in the molten cheese mass 9 being stretched. The stretching is continued until the extended string(s)/sheet 13 of the molten cheese mass 9, connecting both halves 7, 8 of the pizza base is completely broken. Stretch is defined as the distance travelled by the moveable element 2 to the point of complete strand breakage. So as to simulate the way cooked pizza is eaten in practice, the stretch test is performed at room temperature one minute after the pizza pie 10 is removed from the oven.

Figure 2:
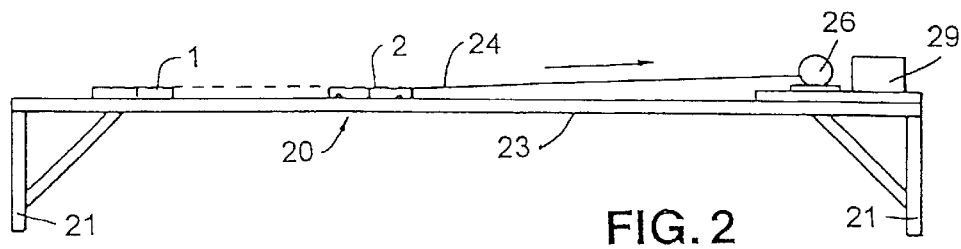
FIG. 2 is a front elevation of the apparatus of FIG. 1 mounted on a frame.
Figure 3:
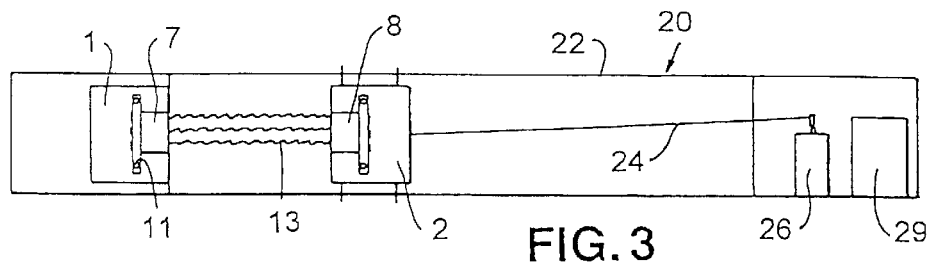
FIG. 3 is a plan view of the apparatus of FIG. 2.
Figure 4:
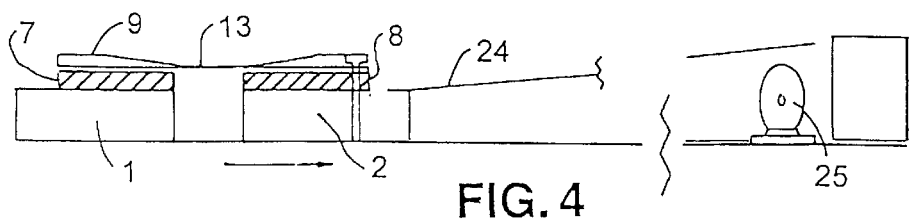
FIG. 4 is a schematic illustration of the stretchability of cheese on a pizza base.

Referring now to FIGS. 2 to 3, these show a practical embodiment of the apparatus of the invention.

The apparatus comprises an elongate support frame 20, having legs 21. The support frame 20 lies in a horizontal plane. Suitably, the support frame 20 comprises two parallel longitudinal rails 22, 23. For example, they may be comprised of suitable lengths of angled steel sections bolted to the legs 21.

A rectangular fixed platform element 1 is fixedly mounted at one end of the support frame 20. For example, the platform element 1, suitably made from stainless steel, may be bolted or otherwise fixedly secured to the frame 20 between the rails 22, 23. A clamp 11 (see FIG. 3) is attached to the platform element 1 by wing nuts or the like, by means of which a pizza base half 7 may be clamped to the platform 1.

A platform element 2 is moveable along the rails 22, 23. The platform element 2 comprises a flat plate, suitably made from stainless steel and has a bogey 14 (see FIG. 7) by means of which it may travel along the rails 22, 23. A clamp 12 (see FIG. 3) is attached to the platform element 2 by wing nuts or the like by means of which a pizza base half 8 may be clamped to the moveable platform 2.

The moveable platform 2 is moved along the rails 22, 23 by means of a cord or wire 24 connected to winch means, driven by a motor 26.

The bogey 14 of the moveable platform element 2 is shown in more detail in FIG. 7. The bogey is similar in design principle to a railway bogey running on twin tracks; friction being kept to a minimum. FIG. 7 shows the underside of the platform element 2. The bogey comprises pairs of complementary axle bearings 15, 16 located adjacent respective corners of the platform element 2. Axles 17, 18 are journalled for rotation in the bearings 15, 16 respectively. Rollers 19 are fixed to the ends of the axles 17, 18 and are adapted to run along the rails 22, 23.

The rollers 19 and complementary rails 22, 23 may have a number of different shapes and configurations.

For example, the rollers 19 may be in the form of flanged wheels running on a narrow rail.

The rollers may be in the form of a cylindrical roller having a groove in the surface thereof which engages with a narrow rail.

In an alternative arrangement as shown in FIGS. 8 to 10 the rails 22, 23 are of circular cross-section and the rollers 19 which engage the rails are formed with a continuous part-circular indent 27 which embraces the circular rail 22, 23.

Figure 11:
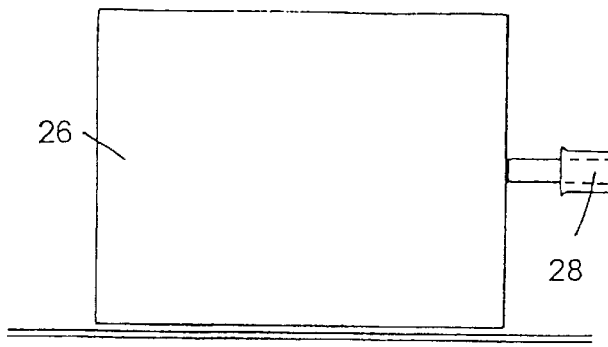
FIGS. 11 and 12, show, respectively, front and side elevations of a motor and pully assembly of the apparatus of FIG. 2.
Figure 12:
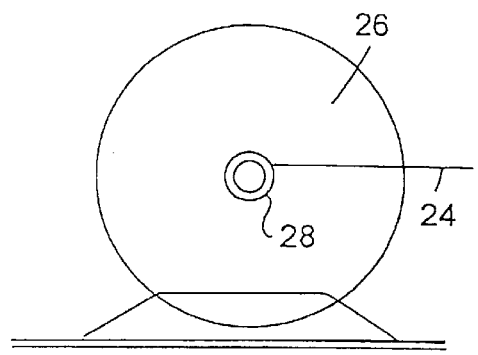

One embodiment of a motor assembly is shown in FIGS. 11 and 12. The assembly comprises an electric motor 26, which drives a pulley 28. The pulley 28 acts as a winch to draw up the cord 24 which is attached to the bogey 14. Typically the motor 26 is a 35 watt motor which runs at a speed of 100 r.p.m. A voltage-to-frequency power converter 29 (see FIGS. 2 and 3) may be connected to the motor to regulate the motor speed, thereby enabling the molten cheese to be stretched at different velocities, the range 2 to 6 m/min.

In operation, the bogey 14 is stopped by switching off the electrical power to the motor 26 driving the winch, via an electrical switch on the voltage-to-frequency power converter 29. Stopping is operated manually upon observation of the point of breakage of the cheese strings. Alternatively, the stopping of the bogey can be fully automated, for example by employing a force transducer which monitors the tensile force during stretching and detects complete breakage when this force disappears.

The distance traveled is measured by graduation on the rails 22, 23 carrying the mobile platform 2. This measurement can be automated using a remote displacement measurement system (e.g. using laser beams) in conjuction with automatic detection of string breakage, as for example the force transducer mentioned above.

Figure 13:
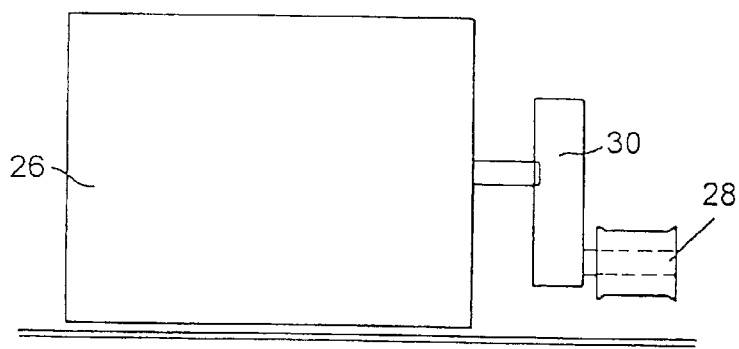
Figure 14:
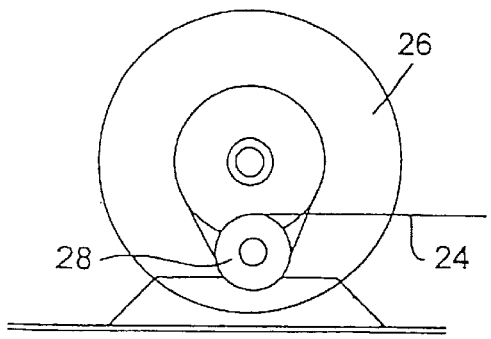

A second embodiment of motor assembly is shown in FIGS. 13 and 14. This assembly is similar to that of FIGS. 11 and 12 and like reference numbers denote like parts. In this embodiment a gearbox 30 is interposed between the motor and the pulley 28, as an alternative to the above described variable speed motor system for applications where only a fixed velocity is required.

Modifications may be made to the apparatus of the invention. For example, the rails 22, 23 may be foldable or telescopic to facilitate storage and transport. A tray (not shown) may be provided to facilitate cooking of the pizza sample. The tray is a rectangular stainless steel tray having side walls of a height approximately twice the thickness of the pizza base. This allows for different cheese loadings and minimizes the risk of cheese falling from the base, on spreading or vibrating, which might otherwise happen. One of the sidewalls is hinged to facilitate removal of the cooked pizza base from the tray. Vibrating means may be provided to vibrate the sample pizza so as to spread the cheese evenly over the base prior to cooking.

Use of the apparatus of the invention to measure the stretchability of cheese is described in the following non-limiting Example.

EXAMPLE

Various experimental and commercial samples of low moisture Mozzarella, Cheddar and analogue pizza-type cheeses were tested (Table 1). Grated cheese samples were analysed in triplicate for moisture, fat, protein, salt, pH, calcium, phosphorous and level of cheese nitrogen soluble in water at pH 4.6 (WSN), as described by Guinee et al. (1994). The analyses are presented in Table 1.

The viscosity of the molten cheese was determined by a modification of the procedure of Kindstedt et al. (1989a). A sample (150 g) of grated cheese was weighted into a tin-foil covered, glass cylinder, placed in a thermostatically controlled water bath (70° C.). After a 50 min tempering period at 70° C., the T-bar spindle (number T-E) mounted on the viscometer (Brookfield, Model DV-II; Brookfield Engineering Laboratories Inc., Stoughton, Mass., USA) was lowered, via a helipath, into the column of molten cheese to a depth of 20 mm.

Figure 15:
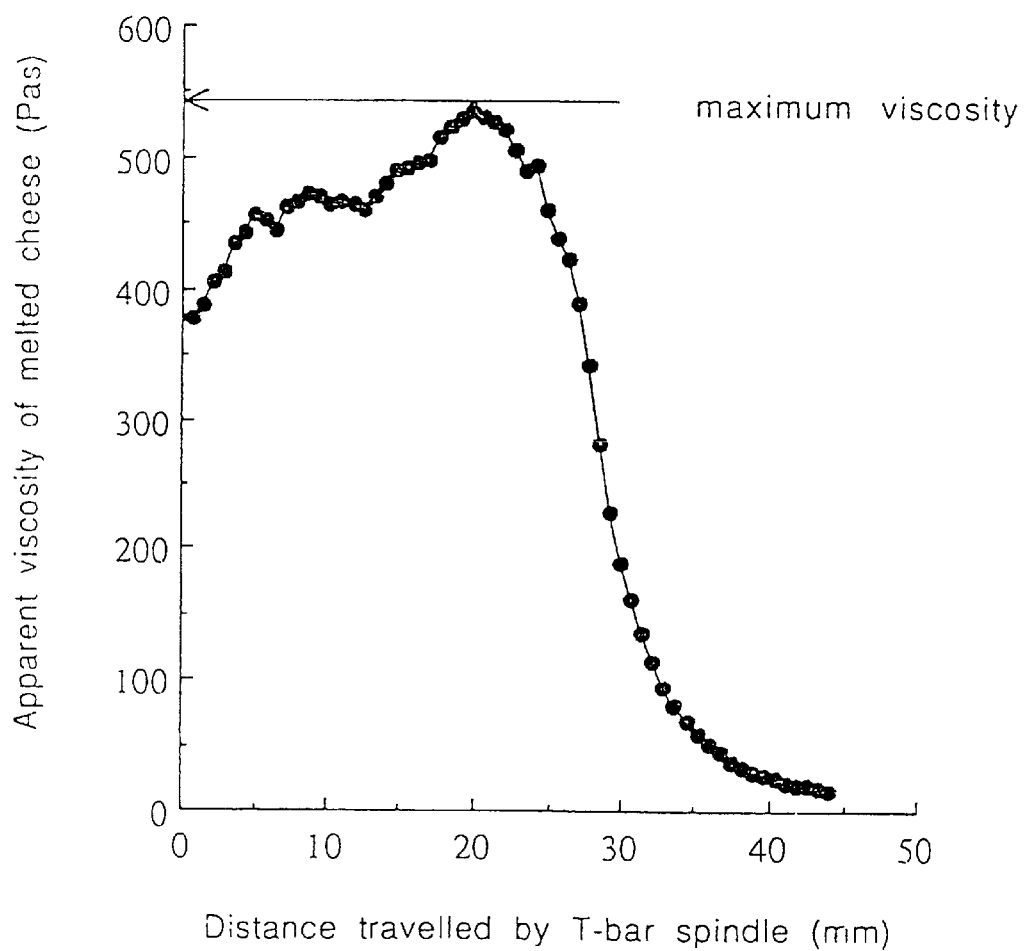
FIGS. 15, 16 and 17 show, respectively, diagrams, I, II and III.

After a 15 mm equilibration period, the viscometer, set at 5 rpm, was activated simultaneously with the helipath. The rotating spindle moved vertically upwards through the molten cheese, at a speed of 22 min/min, for the duration of the 2 min test period. The upward movement of the spindle resulted in a strand of cheese being formed around the spindle at the molten cheese surface. The apparent viscosity, monitored continually at 2 s intervals, was recorded using data-capture software provided by Brookfield. The viscosity increased to a maximum and then decreased as the cheese strand began to fray, and finally dropped markedly as the strand broke as shown in Diagram I in FIG. 15. The analyses were performed in triplicate, and the maximum viscosity was determined.

Measurement of stretchability

Grated cheese was loaded, at a fixed rate on to a rectangular (10.5 cm×15 cm) pizza base. Prior to loading the cheese, the base was cut cleanly in half along the short axis; the halves were aligned in their original position to form a flush interface. Cheese, stored at 4° C., was finely grated (1–2 mm shred length) and distributed evenly over the pizza base and placed in a thermostatically-controlled electric fan oven at 280° C. for 4 min. Fine grating facilitated uniform coverage of the pizza base.

On removal of the cheese from the oven, the stainless steel probe of a digital thermometer was immediately embedded into the mass of molten cheese and the temperature was recorded over time.

The cooked pizza pie was then placed on the platform unit of the stretch apparatus of the invention such that the interface between the two halves of the pizza base coincided with the junction between the fixed and rolling elements. The ends (1.5 cm-strip at the pizza edges) of the pizza were firmly clamped to the platform elements. The rolling element was then drawn along the rail system, at a fixed velocity, by the motor-driven winch system, resulting in the molten cheese mass being stretched. The stretching was continued until the extended string(s)/sheet of the molten cheese mass, connecting both halves of the pizza base, completely broke. Stretch was defined as the distance travelled by the mobile element to the point of complete strand breakage. So as to simulate the way cooked pizza is eaten in practice, the stretch test was performed at room temperature one minute after the pizza pie was removed from the oven.

The standard conditions of stretching, unless otherwise stated, were: cheese loading, 0.25 g/cm² pizza base; stretching velocity, 4 m/min., holding time of melted pizza before stretching, 1 min.

Statistical analysis of stretch measurements

The various series of measurements (e.g. stretch for a given cheese loading) were compared for mean and standard deviation. The significance of difference between means was determined by applying Student's t-test to the statistic $$tm = \frac{\overline{Y}1 - \overline{Y}2}{S_{\overline{Y}1-\overline{Y}2}},$$

where $\overline{Y}_1$ and $\overline{Y}_2$ were the respective means and $S_{\overline{Y}1-\overline{Y}2}$ was the standard deviation appropriate to a difference between random means for a normal population (Steel & Torrie, 1980). The influence of velocity on stretch was tested using linear correlation, by computing $$tr = \frac{r}{\sqrt{(1 - r^2)/(n - 2)}}$$

and comparing with Student's t for n−2 degrees of freedom, where r was the coefficient of correlation between stretch and velocity and n the number of data points.

Results

Effects of various parameters on cheese stretchability

Cheese loading

Increasing the loading of 13-day old, low moisture Mozzarella cheese (A, Table 1) applied to the pizza base, from 0.16 g to 0.25 g/cm², resulted in a significant increase (P<0.001) in the length of stretch obtained using the stretch apparatus of the invention (Table 2). However, varying the cheese load had little influence on the reproducibility of the test with the coefficient of variation amounting to 19–22%. The increase in stretch at the higher loading may be attributed to the increased quantity of molten cheese being fed, from the pizza surfaces, into the stretching fibrous mass between the two pizza halves. Loading rates>0.25 g/cm² were considered unsuitable because of the difficulty in achieving uniform distribution of the cheese, without the cheese falling from the sides of the pizza base.

Stretching velocity

The effect of increasing the stretching velocity from 2 to 6 m/min, on the stretch measurements of 14- and 96- day-old low moisture Mozzarella cheeses (i.e. C and B, Table 1) is presented in Table 3. Similar to the findings of Apostolopoulos (1994) who investigated velocities in the range 0.5 to 1.5 m/min, stretching velocity had no significant influence on stretch length of either cheese. Hence, the slight temperature drop of the cheese during stretching (i.e. 5–6 K over 3 min) had no effect, as the extension velocities were high, i.e. the stretch times were very short, typically ranging from ~9 s at 6 m/min to 21 s at 2 m/min.

Holding time before stretching

Figure 16:
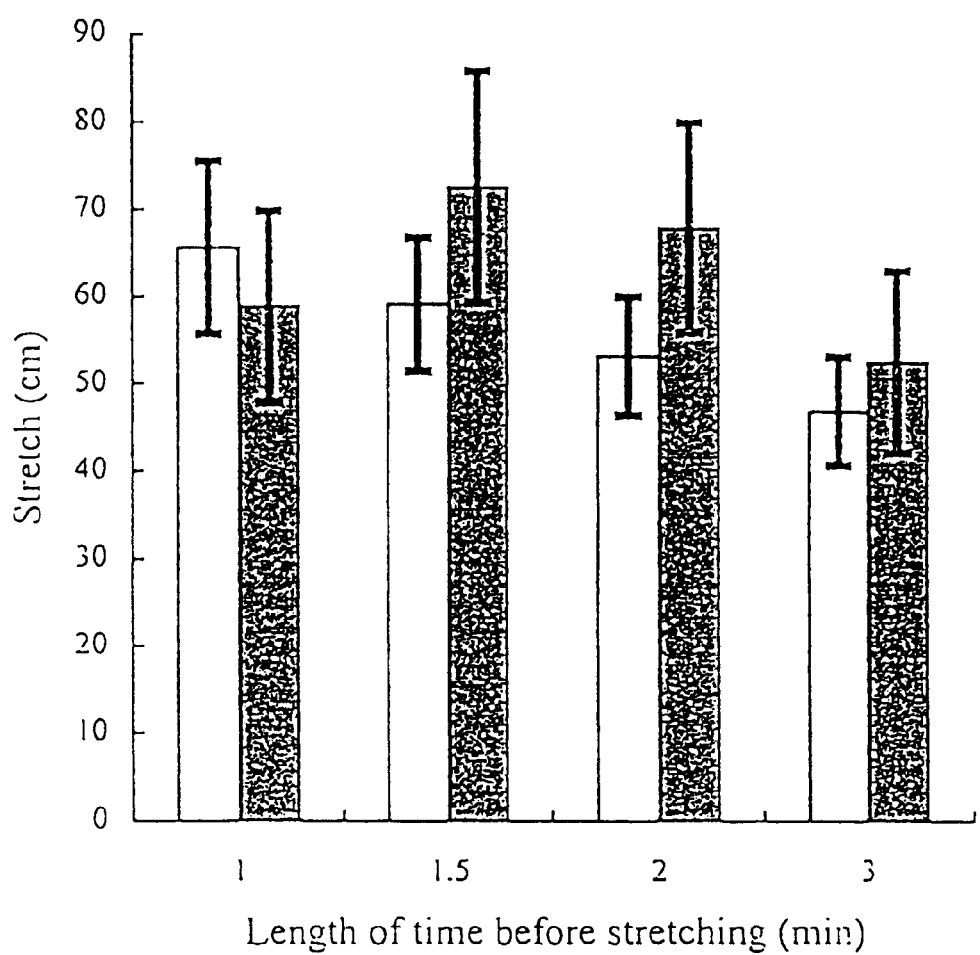

The effects of holding time of the melted pizza pie before stretching on the stretch values obtained from 14- and 96- day-old low moisture cheeses (i.e. C and B, Table 1) are given in Diagram II in FIG. 16. The mean stretchability of the 14 day-old cheese decreased progressively on extending the holding time from 1 to 3 min, with the mean stretch values at holding times of 1 and 1.5 min being significantly higher (P>0.05) than that at the 3 minute holding time. In contrast, the stretch for the 96 day old cheese increased significantly (P<0.05) on extending the holding time from 1 to 1.5 min. A further time increase resulted in a decrease in stretch value, which after 3 min was significantly lower than the corresponding values at holding times of 1.5 (P<0.01) and 2 (P<0.05) min. The general decrease in stretch with holding time was probably due to the drop in temperature (~0.12 K/s over the first 180 s, at the surface of the cooked pizza pie), which results in a partial solidification and stiffening of the molten cheese mass. The different trends observed between the 14 day-, and 96 day-old cheeses on increasing the holding time from 1 to 1.5 min, may be at least partly ascribed to differences in the levels in soluble N (Table 1). Moreover, the apparent viscosity of melted low moisture Mozzarella decreases progressively with proteolysis and ripening time (Kindstedt, 1995; FIG. 5); it is conceivable that melted cheeses with relatively low apparent viscosity require longer times to congeal.

Cheese age

The effects of ripening time on the stretch values for low moisture Mozzarella (cheeses D, E and F, Table 1) and Cheddar (cheeses N and O, Table 1) are shown in Table 4. At 14 days the stretch value for Cheddar was significantly lower than that of low moisture Mozzarella. Surprisingly, increasing the age from 14 days to 119 days had no significant influence on the stretch length of low moisture Mozzarella, even though the increase in ripening time corresponded with a decrease in the level of intact casein, as reflected by the increase the level of soluble N at pH 4.6 (Table 1). In contrast 175-day-old Cheddar cheese had a significantly lower (P<0.01) stretchability length than 14-day-old Cheddar. The different trends of stretch with age may be attributed to differences in the rate of degradation of the paracasein cheese networks, as reflected by the differences in the rate of formation of soluble N (Table 1). Owing to the high temperatures (~58–60° C.) to which the Mozzarella curd is subjected during the texturisation stage of manufacture, residual coagulant activity, which is the main agent responsible for the gross degration of the paracasein, is much lower than in Cheddar (Singh and Creamer, 1990).

Cheese type

The stretch values obtained for a range of retail natural cheeses and analogue pizza cheeses, procured from local factories, were obtained. Considerable inter-category variation existed, with stretch values for block Mozzarella cheeses being generally higher than those of 14-day-old Cheddar cheese. The latter in turn had a significantly higher (P<0.05) value than that of 175-day-old Cheddar or analogue Pizza cheeses. The intra-category variation, observed for Mozzarella and Cheddar, probably reflects differences in the levels of intact paracasein (due to by age), make procedure, and/or composition and to differences in formulation and processing conditions for the analogue pizza cheeses (Table 1).

CONCLUSIONS

The invention provides a simple rapid method, based on uniaxial extension of melted cheese at constant velocity, for the evaluation of the stretchability of cheese on pizza pies, under conditions resembling those applied by the consumer in practice. The stretchability is influenced by the load of cheese per unit area of pizza surface, and by the length of holding time of the pizza before stretching. The extension velocity on the range 2–6 m/min, was found to have little effect on stretchability. The method, which had a coefficient of variation ranging from 10–25%, had the capacity to discriminate between different types of functional cheeses vis-a-vis their stretchability. The optimum conditions of testing may vary with the type and age of cheese, which influence melting properties.

Figure 17:
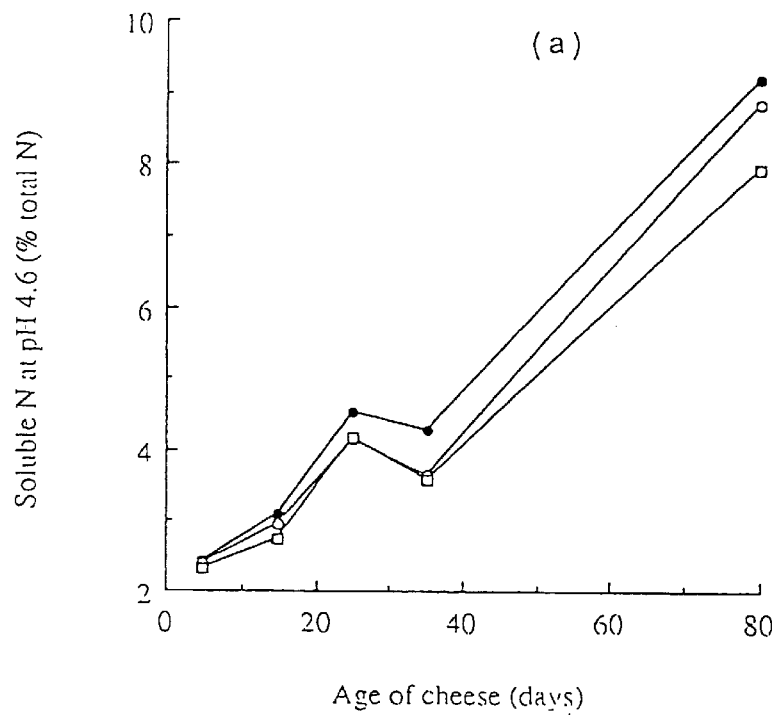
Figure 17:
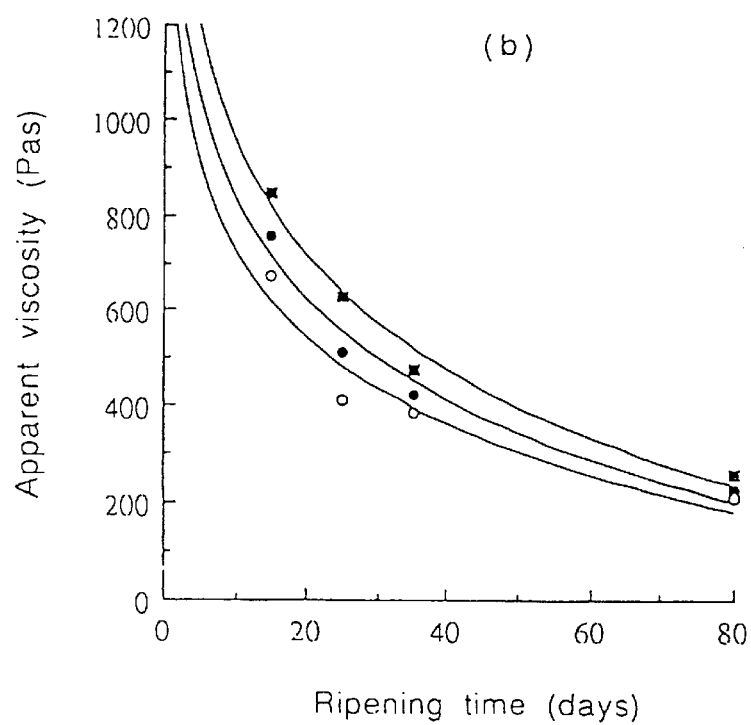

While other extension methods (Pagliarini and Beatrice, 1984; Apostolopoulos, 1994) have measured both force and displacement at fracture of the melted elongated cheese string(s), no relationship was established between yield stress and stretchability. Indeed it has been shown that beyond the yield point the stress remains more or less constant to the point of fracture, suggesting a toughening of the molten cheese string during stretching (Apostolopoulos, 1994). Hence, uniaxial extension of the molten cheese mass to the point of fracture appears to be a realistic measure of stretchability. However, this test does not provide a measure of the consistency, which is perceived as chewiness by the consumer. Apparent viscosity of molten Mozzarella has been used as a measure of its consistency, or chewiness (Kindstedt, 1995). The progressive decrease in apparent viscosity of the molten cheese during ripening reflected the transition from tough chewy and fibrous product to one which is tender and flowable as shown in Diagram III in FIG. 17. Hence, the use of helipath viscometry (Kindstedt et. al., 1989a, 1989b) in conjuction with a uniaxial stretch method of the invention, provides information on two of the more important quality criteria of functional cheeses, namely stretchability and chewiness.

TABLE 1

Compositions of cheeses used for functional analysis†

| Cheese Code/Type | Age‡ (Days) | Table/FIG. | Moisture (% w/w) | Fat (% w/w) | Protein (% w/w) | Salt (% w/w) | N soluble at pH 4.6 (% cheese N) | Ca (mg/g protein) | P (mg/g protein) | pH |
|---|---|---|---|---|---|---|---|---|---|---|
| A. Block Mozzarella | 13 | 2.4/— | 45.6 | 23.0 | 27.3 | 1.2 | 1.8 | 34.4 | ND | 5.65 |
| B. Block Mozzarella | 96 | 3/4 | 44.4 | 24.0 | 28.5 | 1.0 | 11.5 | 28.8 | 20.4 | 5.51 |
| C. Block Mozzarella | 14 | 3/4 | 46.4 | 20.0 | 29.3 | 1.1 | 2.3 | 29.9 | 21.2 | 5.35 |
| D. Block Mozzarella | 14 | 4/— | 45.6 | 23.0 | 27.3 | 1.2 | 1.8 | 34.4 | ND | 5.65 |
| E. Block Mozzarella | 56 | 4/— | 44.5 | 24.3 | 27.7 | 1.3 | 3.3 | 32.1 | ND | 5.60 |
| F. Block Mozzarella | 119 | 4/— | 45.9 | 23.7 | 27.1 | 1.0 | 11.9 | 26.8 | 21.0 | 5.54 |
| G. Block Mozzarella | 5 | —/5 | 48.1 | 22.3 | 26.8 | 1.1 | 2.4 | 26.5 | 20.0 | 5.40 |
| H. Block Mozzarella | 5 | —/5 | 46.3 | 23.9 | 28.0 | 1.0 | 2.7 | 27.1 | 10.7 | 5.46 |
| I. Block Mozzarella | 5 | —/5 | 45.2 | 23.8 | 28.9 | 1.2 | 2.3 | 26.8 | 20.0 | 5.44 |
| J. Analogue pizza Cheese | ? | —/6 | 40.4 | 26.5 | 19.0 | 1.21 | 2.0 | 36.3 | 36.0 | 6.14 |
| K. Analogue pizza Cheese | ? | —/6 | 49.4 | 26.0 | 16.1 | 2.1 | 2.2 | 33.8 | 26.1 | 6.20 |
| L. Analogue pizza Cheese | ? | —/6 | 50.3 | 26.0 | 18.2 | 1.8 | 1.2 | 31.5 | 25.0 | 6.31 |
| M. Grated Cheddar | ? | —/6 | 36.8 | 35.5 | 23.9 | 1.7 | 15.2 | 26.7 | 23.2 | 5.15 |
| N. Block Cheddar | 175 | —/6 | 36.9 | 32.5 | 25.8 | 2.0 | 12.3 | 29.5 | 21.3 | 5.07 |
| O. Block Cheddar | 14 | —/6 | 38.0 | 31.5 | 25.8 | 1.6 | 8.5 | 25.8 | ND | 5.16 |
| P. Grated Mozzarella | ? | —/6 | 44.1 | 23.0 | 29.8 | 0.9 | 1.1 | 25.7 | 19.5 | 5.52 |
| Q. Grated Mozzarella | ? | —/6 | 46.7 | 24.5 | 25.2 | 1.7 | 9.8 | 25.9 | 22.8 | 5.52 |
| R. Block Mozzarella | ? | —/6 | 44.7 | 24.5 | 25.9 | 1.5 | 3.4 | 29.7 | 23.6 | 5.69 |
| S. Block Mozzarella | ? | —/6 | 46.1 | 23.0 | 25.2 | 1.6 | 4.9 | 25.5 | 19.5 | 5.59 |

†Cheeses A–I, N and O are experimental cheeses, all other cheeses are obtained from commercial sources
‡? denotes that the age of commercial cheeses was not known
ND Not Determined

TABLE 2

The effect of cheese loading on the stretch measurements for 13-day old low moisture Mozzarella Cheese (A, Table 1)

| | Stretch, cm | |
| --- | --- | --- |
| Measurement | loading 1 (0.16 g/cm$^2$) | loading 2 (0.25 g/cm$^2$) |
| 1 | 30.0 | 52 |
| 2 | 41.0 | 97 |
| 3 | 34.5 | 72 |
| 4 | 28.5 | 90 |
| 5 | 32.5 | 95 |
| 6 | 47.0 | 90 |
| 6 | 36.0 | 65 |
| 7 | 28.5 | 60 |
| 8 | 45.0 | 90 |
| 9 | 42.0 | 97 |
| 10 | 28.5 | 75 |
| 11 | 22.3 | 60 |
| 12 | — | 77 |
| 13 | — | 76.5 |
| Mean ($\bar{x}$) | 34.7 | 78.3 |
| Standard Deviation ($\sigma$) | 7.7 | 15.1 |
| Coefficient of Variation % | 22 | 19 |

Apart from loading, cheeses were tested under standard conditions, as described in the text.

TABLE 3

Effect of stretch velocity on the stretch measurements, for low moisture Mozzarella cheeses (B, C. Table I).†

| | Velocity (m/min) | | | | | | | |
| --- | --- | --- | --- | --- | --- | --- | --- | --- |
| | 2 | 3 | 4 | 6 | 2 | 3 | 4 | 6 |
| Age of Cheese (Days) | 14 | 14 | 14 | 14 | 96 | 96 | 96 | 96 |
| Measurement | Stretch (cm) | | | | | | | |
| 1 | 54 | 63 | 76 | 77 | 53 | 56 | 49 | 91 |
| 2 | 56 | 78 | 73 | 57 | 60 | 78 | 61 | 68 |
| 3 | 65 | 45 | 89 | 60 | 65 | 55 | 53 | 54 |
| 4 | 55 | 73 | 69 | 79 | 70 | 54 | 80 | 83 |
| 5 | 49 | 56 | 46 | 54 | 60 | 50 | 60 | 50 |
| 6 | 64 | 65 | 78 | 57 | 63 | 64 | 47 | 52 |
| 7 | 58 | 61 | 70 | 80 | 55 | 77 | 68 | 62 |
| 8 | 65 | 62 | 67 | 61 | | 54 | 54 | 49 |
| 9 | 59 | | 70 | 60 | | | 78 | |
| Mean ($\bar{x}$) | 58.3 | 67.8 | 72.0 | 64.1 | 60.6 | 61.5 | 61.1 | 63.6 |
| Standard Deviation ($\sigma$) | 5.5 | 14.6 | 8.9 | 11.8 | 5.9 | 10.4 | 12.0 | 15.9 |
| Coefficient of Variation, % | 9 | 22 | 12 | 18 | 10 | 17 | 20 | 25 |

†Apart from stretching velocity, cheeses were tested under standard conditions, as described in the text.

TABLE 4

The effect of age on the stretch measurements for low moisture Mozzarella and Cheddar, obtained using the stretch apparatus.†

| | Mozzarella‡ | | | Cheddar§ | |
| --- | --- | --- | --- | --- | --- |
| Age(days) | 14 | 56 | 119 | 14 | 175 |
| Measurement | Stretch (cm) | | | | |
| 1 | 52 | 79 | 88 | 51 | 10 |
| 2 | 97 | 60 | 79 | 43 | 19 |
| 3 | 72 | 92 | 69 | 75 | 18 |
| 4 | 90 | 78 | 79 | 72 | 15 |
| 5 | 95 | 89 | 68 | 51 | 16 |
| 6 | 90 | 72 | 67 | | |
| 7 | 65 | 54 | 67 | | |
| 8 | 60 | 69 | 72 | | |
| 9 | 90 | 68 | 75 | | |
| 10 | 97 | 62 | 73 | | |
| 11 | 75 | 74 | 71 | | |
| 12 | 60 | | 75 | | |
| 13 | 77 | | 67 | | |
| 14 | 60 | | 82 | | |
| 15 | | | 74 | | |
| 16 | | | 65 | | |
| 17 | | | 80 | | |
| 18 | | | 91 | | |
| 19 | | | 67 | | |
| 20 | | | 67 | | |
| Mean ($\bar{x}$) | 77.1 | 72.5 | 73.8 | 58.4 | 15.6 |
| Standard Deviation ($\sigma$) | 15.9 | 11.7 | 7.4 | 14.2 | 3.5 |
| Coefficient of Variation, % | 21 | 16 | 10 | 24 | 22 |

†Cheeses were tested under standard conditions, as described in text.
‡Cheeses D, E and F, Table 1.
§Cheeses O and N, Table 1.

What is claimed is:

1. Apparatus for the quantification of the stretchability of molten cheese on a pizza pie, the molten cheese comprising a cooked mass of shredded cheese loaded onto and bridging two separated parts of an underlying pizza base, the apparatus comprising a first platform to receive one part of the pizza base, a second platform to receive the other part of the pizza base, such that the interface between the two parts of the pizza base coincides with a junction between the platforms, means for moving at least one of said platforms relative to the other platform, to draw the two parts of the pizza base apart thereby stretching the m ass of cheese into strands, means for measuring the distance traveled by the second platform relative to the first platform, and clamp means for clamping the parts of the pizza base to the platforms, wherein the one part of the pizza base may be clamped to the first platform and the other part of the pizza base may be clamped to the second platform, and the first platform is a fixed platform and the second platform is moveable along horizontal rails, by electric motor means for causing a uniaxial extension of the melted cheese strands in a horizontal plane at constant velocity to the point of fracture of the strands.

2. The apparatus according to claim 1, wherein the second platform is mounted on a wheeled bogey which may be drawn along the rails by winch means driven by an electric motor at constant velocity.

3. The apparatus according to claim 2, wherein a voltage-to-frequency power converter is connected to the motor to regulate the motor speed such that the molten cheese is stretched at a velocity in the range 2 to 6 m/min.

4. The apparatus according to claim 2, wherein a gearbox is interposed between the electric motor and a pulley of the winch means.

5. The apparatus according to claim 1, wherein the apparatus includes a force transducer which monitors the tensile force applied to the strands of the molten cheese during stretching and detects complete breakage when the force disappears.

6. The apparatus according to claim 5, wherein the measurement means comprises graduation of the rails.

7. A method for the quantification of the stretchability of molten cheese on a pizza pie comprising the steps:

a) slicing a pizza base into two separate parts;

b) loading the adjoined parts of the pizza base with shredded cheese and cooking the pizza in an oven to form a pizza pie in which a molten mass of cheese extends over and bridges the two parts of the pizza base;

c) placing one part of the pizza base on a first platform and a second part of the pizza base on an adjoining platform, such that the interface between the two parts of the pizza base coincides with a junction between the platforms;

d) clamping the respective parts of the pizza base to the respective platforms;

e) moving at least one of said platforms apart relative to the other platform in a horizontal plane at constant velocity to stretch the mass of cheese on the parts of the pizza to form strands which are uniaxially extended, said movement being carried until the cheese strands break;

f) stopping movement of said at least one platform at the point of complete breakage of the cheese stands; and g) measuring the distance travele by the moving platform which equates to the stretch distance of the cheese stands.

8. The method according to claim 7, wherein the method is carried out at room temperature approximately 1 minute after removal of the pizza base from the oven.

9. The method according to claim 8 wherein the pizza is cooked in a thermostatically-controlled electric fan oven.

* * * * *